United States Patent
Smith et al.

(10) Patent No.: US 10,441,311 B2
(45) Date of Patent: Oct. 15, 2019

(54) ATHERECTOMY MEDICAL DEVICE

(71) Applicant: BOSTON SCIENTIFIC SCIMED, INC., Maple Grove, MN (US)

(72) Inventors: Paul Smith, Smithfield, RI (US); Bernard B. Schwartz, East Dorset, VT (US); Samuel Raybin, Marlborough, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 496 days.

(21) Appl. No.: 15/086,965

(22) Filed: Mar. 31, 2016

(65) Prior Publication Data
US 2016/0287284 A1   Oct. 6, 2016

Related U.S. Application Data

(60) Provisional application No. 62/142,139, filed on Apr. 2, 2015.

(51) Int. Cl.
*A61B 17/3207* (2006.01)
*A61B 17/00* (2006.01)
*A61B 17/22* (2006.01)

(52) U.S. Cl.
CPC .......... *A61B 17/320725* (2013.01); *A61B 17/32075* (2013.01); *A61B 17/320758* (2013.01); *A61B 2017/00292* (2013.01); *A61B 2017/00778* (2013.01); *A61B 2017/00867* (2013.01); *A61B 2017/22079* (2013.01); *A61B 2217/005* (2013.01); *A61B 2218/007* (2013.01)

(58) Field of Classification Search
CPC ...... A61B 17/32075; A61B 17/320725; A61B 17/320758
See application file for complete search history.

(56) References Cited

U.S. PATENT DOCUMENTS

| | | | |
|---|---|---|---|
| 5,100,425 | A | 3/1992 | Fischell et al. |
| 5,224,945 | A | 7/1993 | Pannek, Jr. |
| 5,226,909 | A | 7/1993 | Evans et al. |
| 6,183,487 | B1 | 2/2001 | Barry et al. |
| 6,258,109 | B1 | 7/2001 | Barry et al. |
| 6,500,186 | B2 | 12/2002 | Lafontaine et al. |
| 2002/0147458 | A1 | 10/2002 | Hiblar et al. |
| 2013/0116715 | A1* | 5/2013 | Weber ............ A61B 17/320725 606/159 |

FOREIGN PATENT DOCUMENTS

| WO | 0174255 A1 | 10/2001 |
|---|---|---|
| WO | 2013135792 A1 | 9/2013 |

* cited by examiner

*Primary Examiner* — Ashley L Fishback
(74) *Attorney, Agent, or Firm* — Seager, Tufte & Wickhem LLP

(57) ABSTRACT

Medical devices and methods for using medical devices are disclosed. A rotational atherectomy device may include an elongate shaft having a proximal end region, a distal end region and a lumen extending therein. The medical device may also include a cutting member positioned adjacent the distal end region of the elongate shaft. The cutting member may be radially expandable. The medical device may also include a sizing member positioned adjacent the cutting member. The sizing member may be radially expandable, and the radial expansion of the cutting member may be limited by radial expansion of the sizing member.

19 Claims, 10 Drawing Sheets

ATHERECTOMY MEDICAL DEVICE

CROSS-REFERENCE TO RELATED APPLICATIONS

This application claims priority under 35 U.S.C. § 119 to U.S. Provisional Application Ser. No. 62/142,139, filed Apr. 2, 2015, the entirety of which is incorporated herein by reference.

TECHNICAL FIELD

The present disclosure pertains to medical devices, and methods for manufacturing medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

Many patients suffer from occluded arteries and other blood vessels which restrict blood flow. Occlusions can be partial occlusions that reduce blood flow through the occluded portion of a blood vessel or total occlusions (e.g., chronic total occlusions) that substantially block blood flow through the occluded blood vessel. In some cases a stent may be placed in the area of a treated occlusion. However, restenosis may occur in the stent, further occluding the vessel and restricting blood flow. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion.

BRIEF SUMMARY

This disclosure provides design, material, manufacturing method, and use alternatives for medical devices. An example atherectomy device comprises:
an elongate shaft having a proximal end region, a distal end region and a lumen extending therein;
a cutting member positioned adjacent the distal end region of the elongate shaft, wherein the cutting member is radially expandable; and
a sizing member positioned adjacent the cutting member, wherein the sizing member is radially expandable, and wherein radial expansion of the cutting member is limited by radial expansion of the sizing member.

Alternatively or additionally to any of the embodiments above, the sizing member includes one or more struts extending along and away from a central longitudinal axis of the sizing member.

Alternatively or additionally to any of the embodiments above, the sizing member includes a plurality of struts, and wherein the struts are spaced around a central longitudinal axis of the sizing member.

Alternatively or additionally to any of the embodiments above, the sizing member includes a distal tip and a lumen extending therein, and wherein the lumen of the sizing member is in communication with the lumen of the elongate shaft.

Alternatively or additionally to any of the embodiments above, the cutting member includes a plurality of blade members, and wherein the plurality of blade members are spaced around a central longitudinal axis of the cutting member.

Alternatively or additionally to any of the embodiments above, the cutting member includes a plurality of blade members spaced around a central longitudinal axis of the cutting member, and wherein the plurality of blade members are longitudinally aligned with the plurality of struts.

Alternatively or additionally to any of the embodiments above, each blade member is radially expandable independent of the remainder of blade members.

Alternatively or additionally to any of the embodiments above, the struts have an outermost extent, wherein the blade members have an outermost extent, and wherein the outermost extent of the blade members is located closer to the central longitudinal axis than the outermost extent of the struts at any expanded state.

Alternatively or additionally to any of the embodiments above, one or more of the plurality of struts are configured to engage a portion of a vessel wall, and when the one or more of the plurality of struts is engaged with the vessel wall, the blade member aligned with the one or more of the plurality of struts is spaced radially away from the vessel wall a predetermined distance.

Alternatively or additionally to any of the embodiments above, further including a plurality of base members, wherein each base member includes at least one strut and at least one blade member, and wherein each base member is configured to radially flex independently of the other base members.

Alternatively or additionally to any of the embodiments above, further including one or more aspiration ports, wherein the one or more aspiration ports are in communication with the lumen of the elongate shaft.

Alternatively or additionally to any of the embodiments above, further including one or more aspiration ports positioned adjacent the cutting member.

Alternatively or additionally to any of the embodiments above, further including one or more aspiration ports positioned at the distal end region of the elongate shaft, wherein the cutting member includes a lumen extending therein, and wherein the aspiration ports are in communication with the lumen of the cutting member.

Alternatively or additionally to any of the embodiments above, the lumen of the elongate shaft is sized to receive a guidewire or dilator therein when the atherectomy device is advanced over the guidewire or dilator.

Alternatively or additionally to any of the embodiments above, the cutting member includes a cutting edge, wherein the cutting edge extends substantially around the circumference of the cutting member.

Alternatively or additionally to any of the embodiments above, the cutting member has an outermost extent, wherein the sizing member has an outermost extent, and wherein the different between the outermost extent of the sizing member and the outermost extent of the cutting member is constant.

Another atherectomy device comprises:
an elongate shaft having a proximal end region, a distal end region and a lumen extending therein;
a cutting member positioned adjacent the distal end region of the elongate shaft, wherein the cutting member is radially expandable and has an outermost radial extent; and
a sizing member positioned adjacent the cutting member, wherein the sizing member is radially expandable and has an outermost radial extent, and wherein the atherectomy device includes a radial offset, wherein the radial offset is defined as the difference between the outermost radial extent of the cutting member and the outermost radial extent of the sizing member.

Alternatively or additionally to any of the embodiments above, the sizing member includes a plurality of struts, wherein the struts are spaced around a central longitudinal axis of the sizing member, and wherein the cutting member includes a plurality of blade members, and wherein the plurality of blade members are spaced around a central longitudinal axis of the cutting member.

Alternatively or additionally to any of the embodiments above, the plurality of struts are longitudinally aligned with the plurality of blade members.

Alternatively or additionally to any of the embodiments above, the radial offset between the plurality of struts and the plurality of blade members is constant.

Alternatively or additionally to any of the embodiments above, one or more of the longitudinally aligned struts and blade members can flex independently of the remaining struts and blade members.

Alternatively or additionally to any of the embodiments above, the radial offset is defined such that the outermost extent of the cutting member is positioned closer to the central longitudinal axis of the cutting member than the outermost extent of the sizing member.

Another atherectomy device comprises:

an elongate shaft having a proximal end region, a distal end region and a lumen extending therein;

a sizing member positioned adjacent the distal end region of the elongate shaft, wherein the sizing member is radially expandable;

a cutting member positioned adjacent the sizing member, wherein the sizing member is radially expandable, and wherein radial expansion of the cutting member is limited by radial expansion of the sizing member; and one or more channels extending between the elongate shaft, the sizing member and the cutting member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
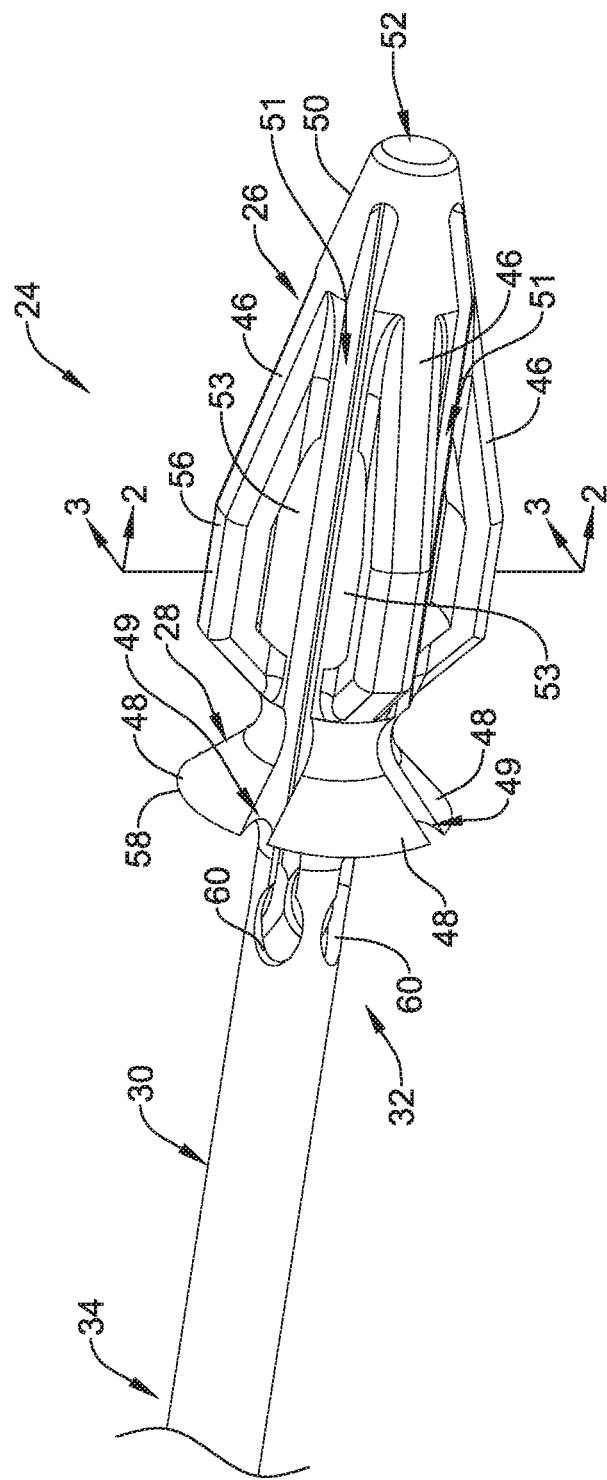
FIG. 1 is a perspective view of an example medical device.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Many patients suffer from occluded arteries, other blood vessels, and/or occluded ducts or other body lumens which may restrict bodily fluid (e.g. blood, bile, etc.) flow. Occlusions can be partial occlusions that reduce blood flow through the occluded portion of a blood vessel or total occlusions (e.g., chronic total occlusions) that substantially block blood flow through the occluded blood vessel. Revascularization techniques include using a variety of devices to pass through the occlusion to create or enlarge an opening through the occlusion. Atherectomy is one technique in which a catheter having a cutting element thereon is advanced through the occlusion to form or enlarge a pathway through the occlusion. Ideally, the cutting element excises the occlusion without damaging the surrounding vessel wall and/or a previously implanted stent where restenosis has occurred. However, in some instances the cutting element may be manipulated and/or advanced such that it contacts the vessel wall and/or the stent. Therefore, it may be desirable to utilize materials and/or design an atherectomy device that can excise an occlusion without damaging the surrounding vessel and/or a previously implanted stent where restenosis has occurred. The methods and systems disclosed herein are designed to overcome at least some of the limitations of atherectomy devices that could damage vessels and/or implanted stents while excising occlusive material. For example, some of the methods disclosed herein may include utilizing a sizing member to control the radial expansion of a cutting member.

FIG. 1 shows an example atherectomy device 24 including an elongate shaft 30 coupled to a cutting member 28. Cutting member 28 may further be coupled to, arranged with, or otherwise adjacent to a sizing member 26. Elongate shaft 30 may include a distal end region 32 and a proximal end region 34. As shown in FIG. 1, the cutting member 28 may be positioned at the distal end region 32 of elongate shaft 30.

The distal end region of elongate shaft 30 may include one or more aspiration ports 60 positioned adjacent blade members 48 of cutting member 28. As shown in FIG. 1, aspiration ports 60 may extend through the wall of the elongate shaft 30 and be in communication with a vessel within which atherectomy device 24 is positioned.

Aspiration ports 60 may be shaped in a variety of configurations. For example, FIG. 1 shows aspiration ports 60 shaped in a generally ovular configuration. However, in other embodiments, aspiration ports may be circular, square, triangular or the like.

Additionally, FIG. 1 shows aspiration ports 60 spaced around a central longitudinal axis of elongate shaft 30. In some instances, aspiration ports 60 may be spaced equidistant around a central longitudinal axis of elongate shaft 30. However, other spacing configurations are contemplated.

In some instances, cutting member 28 may be attached to the distal end region 32 of elongate shaft 30. Cutting member 28 may include individual cutting blades 48 (as shown in FIG. 1). For example, cutting member 28 may include a first, a second, a third and/or a fourth cutting blade. Further, individual cutting blades 48 may have an outermost cutting extent 58. Cutting blades 48 may include a cutting edge, such as along the outermost cutting extent 58. The cutting edge may define an arcuate path along a portion or all of one or more of the cutting blades 48. Further, the arcuate path of the cutting edge of each cutting blade 48 may include an arc length that extends substantially around a portion of the circumference of cutting member 28. In some instances, the cutting edge may be defined along the outermost cutting extent 58 for one or more of cutting blades 48. However, it is contemplated that the cutting edge may be defined along any portion of cutting blades 48. FIG. 1 shows individual cutting blades tapering in a proximal to distal direction from the outermost extent 58.

In some examples, cutting member 28 may have a plurality of cutting blades 48 spaced apart from one another, such as symmetrically arranged around a central longitudinal axis of the cutting member 28. For example, in some instances cutting member 28 may include four individual cutting blades 48 spaced equidistant from each other around a central longitudinal axis of cutting member 28. It is contemplated, however, that cutting member 28 may include more or less than four cutting blades 48 in other embodiments. For example, cutting member may include 2, 3, 4, 5, 6, 7, 8, 9, 10, 20 or more cutting blades 48.

Additionally, as shown in FIG. 1, the spacing 49 between individual cutting members 48 may align with aspiration ports 60. In other words, the spacing 49 between individual cutting members 48 may resemble "channels" that align with aspiration ports 60. In some instances, the channels 49 may be in fluid communication with a central lumen 64 (shown in FIG. 3) of the cutting member 28. Further, channels 49 along with central lumen 64 may be in fluid communication with lumen 54 (shown in FIG. 3) of elongate shaft 30.

The catheter 24 may also include a sizing member 26 arranged proximate to the cutting member 28. For instance, the sizing member 26 may be positioned adjacent to the cutting member 28, either proximal of the cutting member 28 or distal of the cutting member 28. As illustrated in FIG. 1, the sizing member 26 may be located distal of the cutting member 28, with a distal end region of cutting member 28 attached to a proximal end region of sizing member 26.

Sizing member 26 may include individual strut members 46 that extend along sizing member 26. For example, sizing member 26 may include a first, a second, a third and/or a fourth strut member 46. In some examples, a first strut 46 may longitudinally align with a first cutting blade 48, a second strut 46 may longitudinally align with a second cutting blade 48, a third strut 46 may longitudinally align with a third cutting blade 48 and/or a fourth strut 46 may longitudinally align with a fourth cutting blade 48. Further, in some examples individual strut members 46 may extend outward and/or away from the central longitudinal axis of sizing member 26.

Similar to the above discussion with respect to cutting blades 48, individual struts 46 may have an outermost extent 56. Further, FIG. 1 shows individual strut members 46 having a general arcuate shape, with the outermost extent 56 positioned generally midway along individual strut member 46. The shape of strut members 46 shown in FIG. 1 is just an example. Other shapes are contemplated. For example, individual strut members 46 may include combinations of straight portions alone or in combination with arcuate portions. Furthermore, the outermost extent 56 may be located along any portion of strut member 46.

In some instances (e.g. as shown in FIG. 1), the spacing 51 between individual strut members 46 (also shown in FIG. 2) may align with aspiration ports 60 and channels 49 of cutting member 28. In some instances, the spacing 51 between struts 46 may be in communication with a central lumen 62 of the sizing member 26 and/or the central lumen 64 of the cutting member 28 and the central lumen 54 of elongate shaft 30 (lumens 62, 64 and 54 are shown in FIG. 3).

The catheter 24 may include a distal tip 50 positioned at a distal end region of sizing member 26. The distal tip 50 may include lumen 52. Lumen 52 may be in communication with lumen 62 of the sizing member 26, the lumen 64 of the cutting member 28 and/or the lumen 54 of the elongate shaft 30 (lumens 52, 62, 64 and 54 are shown in FIG. 3). The lumen 52 of the distal tip 50, along with lumens 62, 64 and 54 may accommodate a guidewire therethrough during a medical procedure.

In some instances, sizing member 46 may include a base member 53 that includes at least one individual strut 46 and at least one blade member 48 of the cutting member 28. In some examples, the strut 46 and blade member 48 associated with a particular base member 53 may be longitudinally aligned with one another and extend radially away from base member 53. For instance, a first strut 46 may be fixed with a first cutting blade 48 via a first base member 53 to form a first unit, a second strut 46 may be fixed with a second cutting blade 48 via a second base member 53 to form a second unit, a third strut 46 may be fixed with a third cutting blade 48 via a third base member 53 to form a third unit, and/or a fourth strut 46 may be fixed with a fourth cutting blade 48 via a fourth base member 53 to form a fourth unit. Accordingly radial expansion/contraction of the first strut 46 may subject the first cutting blade 48 to corresponding radial expansion/contraction, radial expansion/contraction of the second strut 46 may subject the second cutting blade 48 to corresponding radial expansion/contraction, radial expansion/contraction of the third strut 46 may subject the third cutting blade 48 to corresponding radial expansion/contraction, and/or radial expansion/contraction of the fourth strut 46 may subject the fourth cutting blade 48 to corresponding radial expansion/contraction, with radial expansion/contraction of each strut/cutting blade pair being independent of the remainder of the strut/cutting blade pairs.

Figure 2:
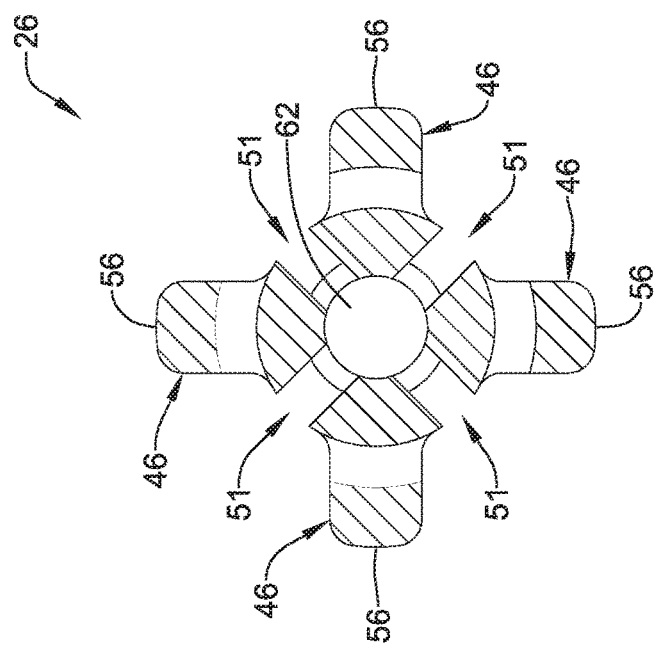
FIG. 2 is a transverse cross-sectional view of the example medical device of FIG. 1 taken along line 2-2 of FIG. 1.
Figure 3:
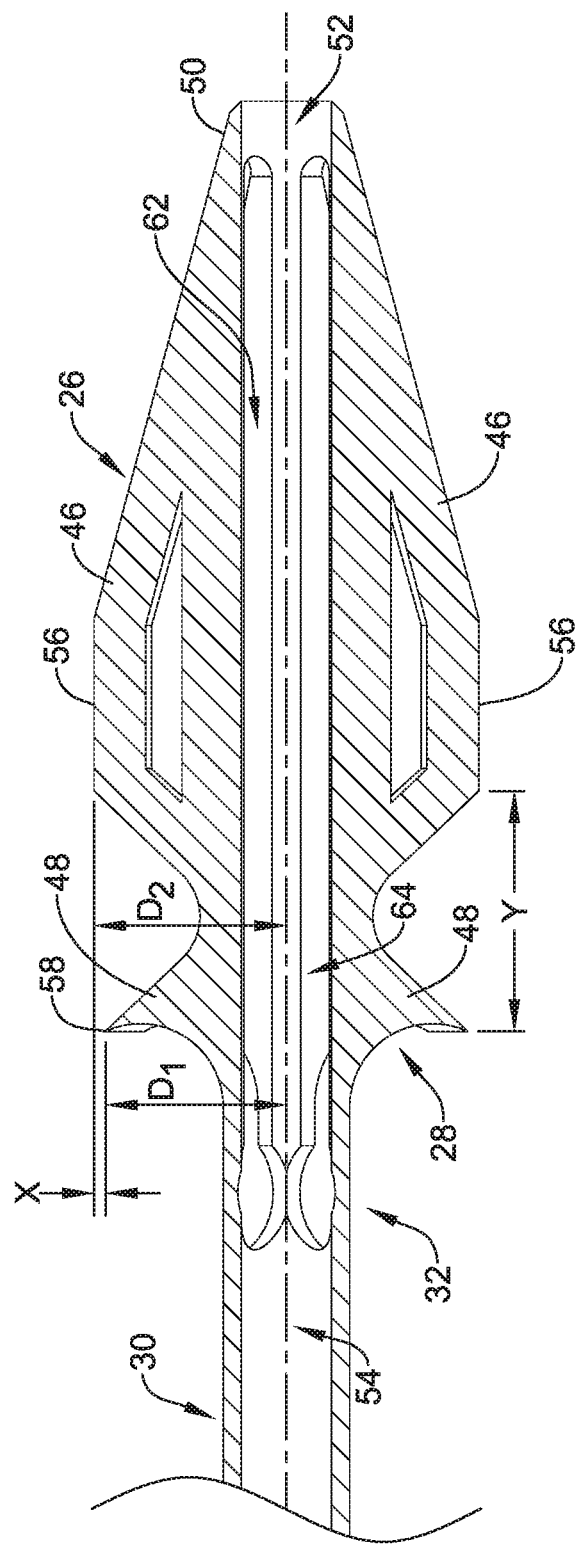
FIG. 3 is a longitudinal cross-sectional view of the example medical device of FIG. 1 taken along line 3-3 of FIG. 1.

FIG. 2 is a cross-sectional view along line 2-2 in FIG. 1. FIG. 2 shows struts 46 of sizing member 26 spaced apart from one another around a central lumen 62 of sizing member 26, with spaces or channels 51 arranged between adjacent struts 46. For example, in some instances sizing member 26 may include four individual struts 46 spaced equidistant from each other around a central longitudinal axis of sizing member 26. This is just an example. It is contemplated that sizing member 26 may include more or less than four struts 46. For example, sizing member may include 2, 3, 4, 5, 6, 7, 8, 9, 10, 20 or more struts 46. Further, FIG. 2 shows the outermost extent 56 of sizing member 26.

FIG. 3 is a longitudinal cross-section along line 3-3 in FIG. 1. As shown in FIG. 3, the outermost extent 56 of individual strut members 46 may be a greater distance away from the central longitudinal axis of atherectomy device 24 as compared to the distance that the outermost extent 58 of cutting member 28 is away from the central longitudinal axis of atherectomy device 24. For example, FIG. 3 shows distance D2 (distance of outermost extent 56 from the central axis) greater than distance D1 (distance from outermost extent 58 from the central axis). In other words, a constant "radial offset" (shown as "X" in FIG. 3) may be maintained between the outermost extent 56 of the strut 46 and outermost extent 58 of the blade member 48. Furthermore, it is contemplated that radial movement of a strut 46 results in corresponding radial movement of the associated blade member 48 of the cutting member 28. Thus, as the strut 46 moves radially outward, the associated blade member 48 moves radially outward an equivalent amount and/or as the strut 46 move radially inward, the associated blade member 48 moves radially inward an equivalent amount. Thus, when a strut 46 is deflected inward, the corresponding blade member 48 may correspondingly move inward so that the amount of radial offset ("X") remains substantially fixed.

In other words, the outermost extent of an example strut 46 may extend outward in a radially direction such that it contacts the vessel wall and/or the inner surface of a stent. However, it is contemplated that the distance that an individual blade member 48 longitudinally aligned with the example strut 46 (e.g. the blade and strut shown in FIG. 3) may radially extend may be slightly less than the distance for which the strut 46 extends at any radially expanded state. Thus, radial expansion of the blade member 48 of the cutting member 28 is limited by radial expansion of the associated strut 46 of the sizing member 26.

Therefore, a strut 46 longitudinally aligned with a blade member 48 (e.g. a strut and blade member aligned along a common base member) may limit the blade member 48 from expanding radially the distance the strut 46 expands away from the central longitudinal axis. Therefore, a strut member 46 may limit and/or prevent a blade member 48 from contacting surfaces which the sizing member 26 may contact. In other words, when the sizing member 26 is contacting the vessel wall or an inner surface of a stent, the outermost extent 58 of the individual blades 48 of cutting member 28 may not extend to the vessel wall or to the inner surface of the stent.

Further, some embodiments may define additional relationships between cutting member 28 and sizing member 26. For example, in some instances the longitudinal distance (shown in FIG. 3 as "Y") between blade member 48 and strut 46 may work in tandem with radial offset "X" to control the radial expansion of cutting member 28 and/or sizing member 26. The longitudinal distance "Y" may be selected to arrange sizing member 26 in close proximity of cutting member 28 such that adjustment in the size of the cutting member 28 closely follows variations in the lumen diameter. Accordingly, longitudinal distance "Y" and the radial offset "X" may be selected relative to one another to provide a desired configuration. The selected distances "X" and "Y" may better control the extent to which cutting member 28 expands and follows the variations in the lumen diameter. In some instances, the radial offset "X" may be about 0.05 mm to 2 mm, about 0.1 mm to 2 mm, or about 0.5 to 2 mm, for example. In some instances, the distance "Y" may be about 1 mm to about 20 mm, about 1 mm to about 10 mm, about 2 mm to about 10 mm, or about 5 mm to about 20 mm, for example. While FIG. 3 shows distances "X" and "Y" to be fixed, it is contemplated that in some instances the distances may be adjustable. For example, a clinician may be able to customize distances "X" and "Y" based on anatomical considerations (e.g. the size, shape curvature and/or type or lesion and body lumen).

The ability and/or relationship of the maximum radially extent of a strut 46 versus a blade member 48 may act to prevent individual blade members 48 from excising, cutting, scraping and/or damaging body structures (e.g. body lumens) or medical devices (e.g. implanted stents). For example, when used in a pull configuration (discussed further below), a physician may deploy an atherectomy device 24 distal to a lesion located within a blood vessel and/or a stent. The physician may draw the atherectomy device 24 in a proximal direction toward the lesion/stent combination. It can be appreciated that as atherectomy device 24 travels along the body lumen and enters the stent, sizing member 26 will initially contact the vessel wall (when outside the stent) and flex inward to contact the inside of the stent (when drawn within the stent). Correspondingly, the outermost extent 58 of blade members 48 of the cutting member 28 will not contact the vessel wall (when outside the stent) or the inside of the stent (when drawn within the stent) due to the constant radial offset (e.g. "X" in FIG. 3) maintained between the struts 46 and blade members 48. It is appreciated, however, that blade members 48 may excise the portion of the lesion that extends into the body lumen beyond the stent wall. In other words, blade members 48 may excise that portion of a lesion which is within the outermost radial extent 58 of the blade member 48 while not damaging the inner surface of the stent (as it does not contact the inner surface of the stent).

In some instances, it may be desirable for individual base members 53 (including blade members 48 and struts 46) to move, e.g., flex or deflect, (e.g. radially inward and outwardly) independently of one another. Independent flexing of the blade members 48 may allow atherectomy device 24 to excise a lesion (or navigate through a stent) having uneven contours. For example, in some instances atherectomy device 24 may encounter a narrowing when advanced through the vasculature. Upon encountering the narrowing, an individual strut 46 may flex independently of the other struts 46 to navigate the narrowing. Blade members 48 aligned with strut members 46 may maintain a constant offset with the strut member 46 and move, e.g., flex or deflect, correspondingly.

Further, FIG. 3 shows elongate shaft 30 including lumen 54 extending in a proximal direction from distal end region 32. Lumen 54 may extend along a portion, or alternatively, the entire length of elongate shaft 30. Lumen 54 may be sized to accept a guidewire and/or dilator. In some instances, lumen 54 may additionally or alternatively be an aspiration lumen. For example, lumen 54 may be sized such that tissue and/or portions of an excised lesion, for example, may be suctioned through lumen 54 to an exit port located outside the body of a patient.

Additionally, the alignment of the channels 49 with aspiration ports 60, central lumen 64 of cutting member 28 and central lumen 54 of the elongate shaft 30 may provide a generally free-flowing path for tissue (e.g. lesion material) to be aspirated after having been excised by cutting blades 48.

Atherectomy device 24 may be operated in various configurations. For example, in some examples the device 24 may be utilized in a "pull" configuration, whereby the atherectomy device is deployed in a compact configuration distally beyond a target site and withdrawn proximally back through the target site. Other examples depict other devices which may be similar in form and function to other devices disclosed herein. For example, in some examples the atherectomy device 24 may be utilized in a "push" configuration, whereby the device 24 is deployed proximal a lesion and pushed and/or advanced distally through a target site.

FIGS. 4-7 show exemplary aspects of a method of using an example atherectomy device 24 utilized in a "pull" configuration. In some examples atherectomy device 24 may be advanced through an occlusion within a body lumen (e.g., a blood vessel), which in some instances may be an occlusion within a stent member previously placed in an example body lumen. For example, a lesion may develop within a stent member previously deployed in a body lumen. In that case, the cutting member 28 and the sizing member 26 of the atherectomy device 24 may be advanced through both the stent member and the occlusion (which has developed within the stent member) to a location distal of the occlusion, and thereafter withdrawn proximally to remove the occlusion with the atherectomy device 24.

Figure 4:
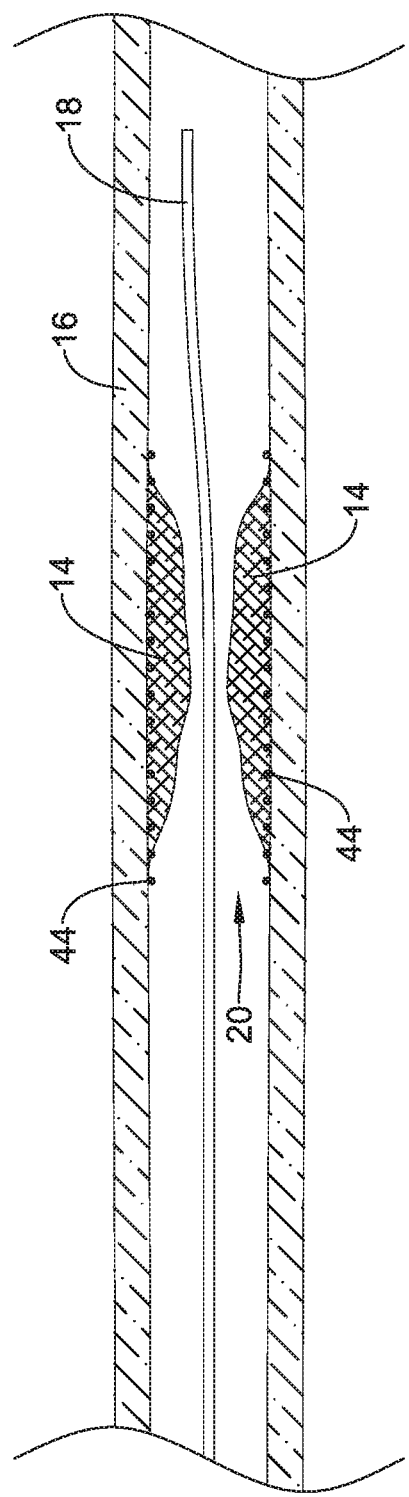
FIGS. 4-7 illustrate aspects of an exemplary method of treating an occlusion at a target site with the medical device of FIG. 1.

FIG. 4 shows an example target lesion 14 and example stent 44 located inside example body lumen 16. Additionally, FIG. 4 shows target lesion 14 developed within stent 44. In some instances, an initial step to treating and/or removing lesion 14 may include passing a guidewire 18 across the lesion 14. FIG. 4 shows guidewire 18 placed through opening 20 in lesion 14 and extending along the entire length of lesion 14.

Figure 5:
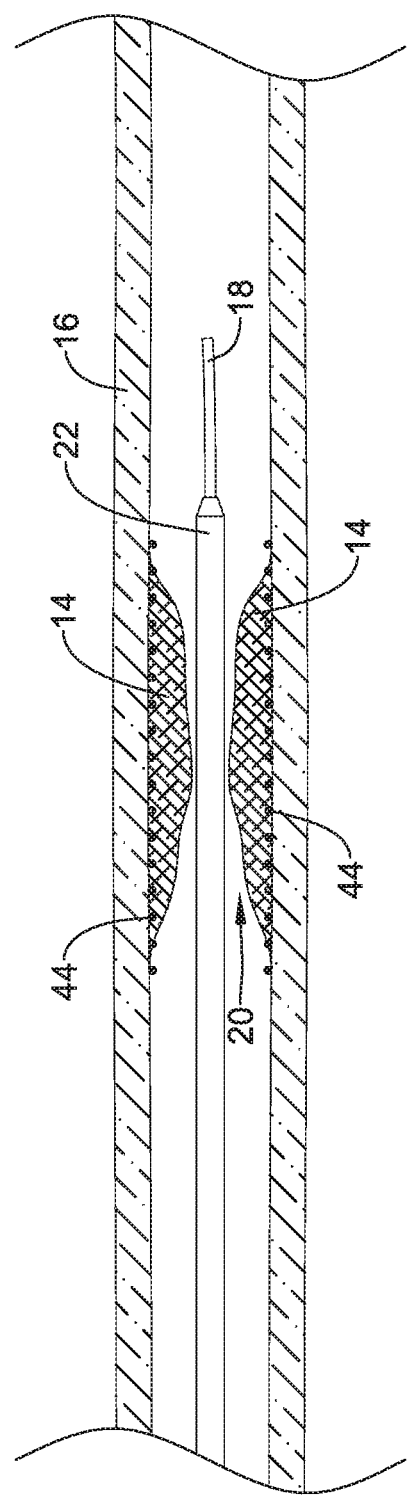

In some instances, a dilator 22 may be used alone or in combination with guidewire 18 to cross lesion 14. For example, FIG. 5 shows example dilator 22 placed across target lesion 14 located inside example body lumen 16. Dilator 22 may be placed through opening 20 in lesion 14 and extend along the entire length of target lesion 14. In some instances dilator 22 may include a lumen extending along a portion or the entire length of dilator 22 through which the guidewire 18 extends. As stated, dilator 22 may be used in combination with guidewire 18 to be placed across lesion 14 (as shown in FIG. 5). For example, in some instances dilator 22 may be tracked along guidewire 18 to reach and advance through target lesion 14. Additionally, dilator 22 may be utilized to provide additional stiffness, column strength, etc. to guidewire 18 and/or atherectomy device 24 advanced thereover.

Figure 6:
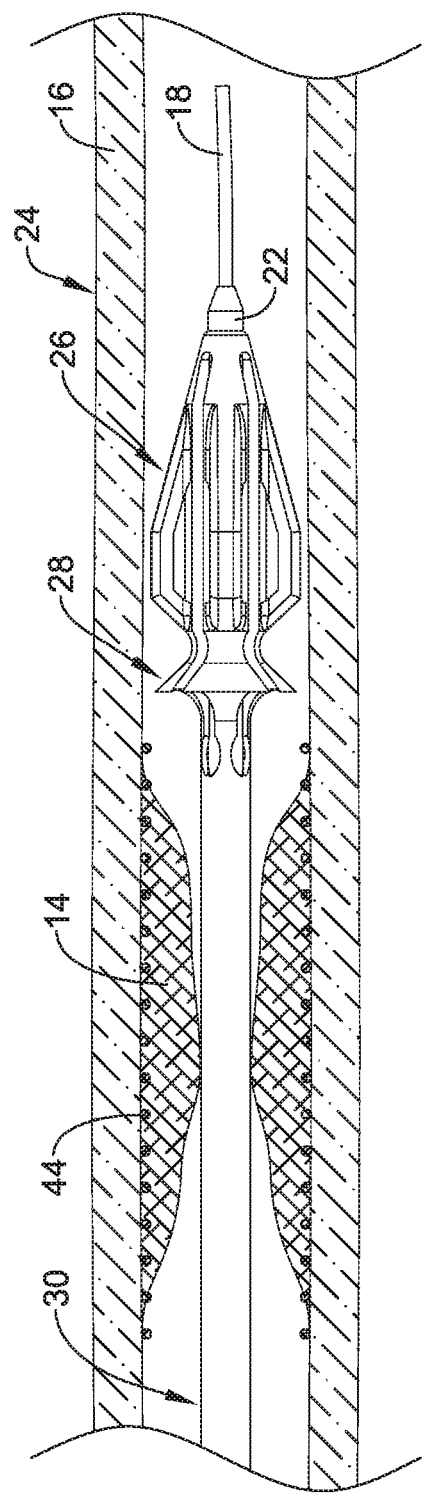

FIG. 6 shows atherectomy device 24 positioned distal to example lesion 14. In FIG. 6, atherectomy device 24 has been advanced and/or tracked along guidewire 18 and/or dilator 22 to the position shown. While not shown in FIG. 6, it can be appreciated that atherectomy device 24 may be delivered to lesion 14 in an unexpanded or collapsed configuration. The unexpanded configuration may reduce the profile of atherectomy device 24 to facilitate crossing lesion 14 in a proximal to distal direction. Once advanced distal of the lesion 14, the dilator 22, if present, may be withdrawn from the lumen of the atherectomy device 24, allowing the lumen to be used as an aspiration lumen, if desired.

Further, once positioned distal to a lesion 14 and/or stent 44 (or, for example, a lesion developed within a stent), the cutting member 28 and sizing member 24 may be radially expanded to an expanded configuration. In the radially expanded configuration, the sizing member 24 may engage the inner surface of the body lumen 16, and thereby prevent further radial expansion of the cutting member 28. Thereafter, the atherectomy device 24 may be pulled and/or drawn in a proximal direction back through the lesion 14 and/or stent 44. As stated above, sizing member 26 may limit the radial expansion of cutting member 28. For example, sizing member 26 may limit the radial expansion of cutting member 28 such that cutting member 28 (when drawn through a lesion developed within a stent) may excise the lesion 14 without damaging the stent 44.

For example, a physician may manipulate a proximal portion of elongate shaft 30 and pull atherectomy device 24 in a distal to proximal direction toward and through the lesion 14. In other words, a physician manipulating atherectomy device 24 may draw cutting member 28 closer and in contact with lesion 14. Further, as cutting member 28 is drawn closer to lesion 14, sizing member 26 may limit the radial expansion of cutting member 28 such that cutting member 28 does not contact any portion of the stent 44 and/or does not expand to a diameter greater than an inner diameter of the stent 44. Thus, the sizing member 26 may limit expansion of the cutting member 28 to a diameter less than an inner diameter of the stent 44.

Figure 7:
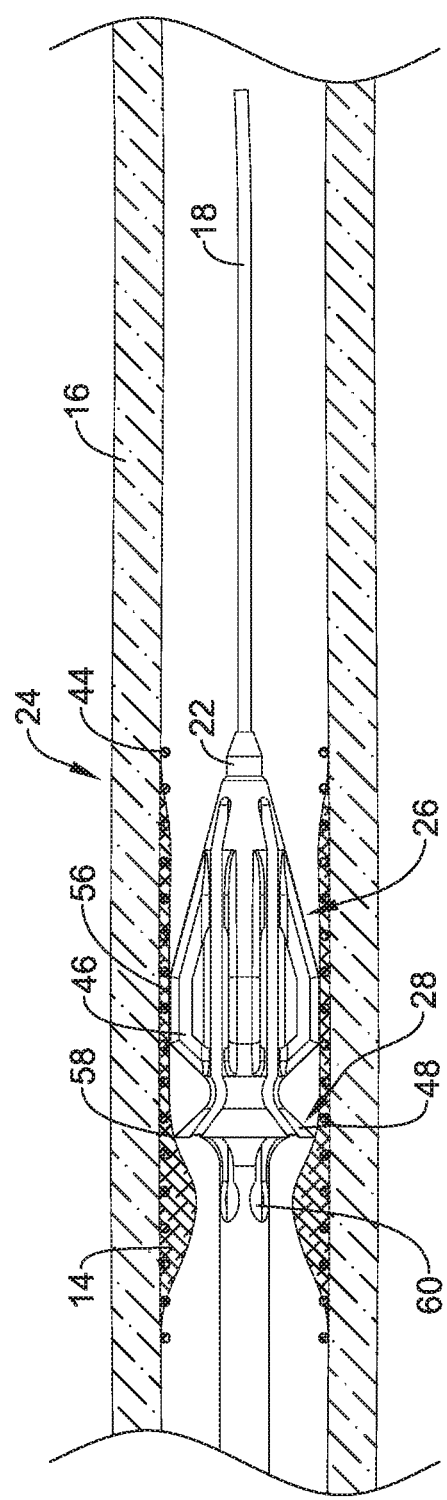

FIG. 7 shows atherectomy device 24 after having been pulled and/or drawn in a proximal direction into example stent 44. Further, FIG. 7 shows cutting member 28 positioned along example lesion 14 (and within example stent 44). As can be appreciated from FIG. 7, cutting member 28 has cut and/or excised a portion of example lesion 14. Furthermore, FIG. 7 shows the outermost extent 56 of strut member 46 positioned against the inner surface of stent 44. As described above and shown in FIG. 7, the outermost extent 58 of example cutting blade 46 extends to a position radially inward from the interior surface of stent 44. In other words, the radial expansion of cutting member 28 is limited by sizing member 26 to a diameter less than the inner diameter of the stent 44.

In some instances (such as that shown in FIG. 7), sizing member 26 may be positioned distal to cutting member 28 during a cutting procedure. Further, cutting member 28 may engage, enter, and/or pass through an occlusion and/or stent before the trailing sizing member 26 engages, enters and/or passes through the occlusion and/or stent. Thus, sizing member 26 may engage a portion of the vessel not obstructed by the occlusion and/or a portion of the vessel in which the occlusion has already been removed (by the cutting member 28, for example) to control the size of the cutting member 28 to an appropriate diameter.

In some instances, the cutting member 28 may be rotated as the cutting member 28 is drawn through the lesion 14, such as by rotating the elongate shaft 30 and/or a drive shaft passing through the elongate shaft 30. In other instances, no rotation of the cutting member 28 may be performed while passing the cutting member 28 through the lesion 14.

Additionally, atherectomy device 24 may aspirate excised tissue as the device 24 is advanced through the vasculature. For example, as shown in FIG. 7, as cutting member 28 cuts and/or excises tissue while being pulled through lesion 14, excised tissue may be sucked into aspiration ports 60. Further, the excised tissue may travel through inner lumen 54 (which, as described above, is in communication with aspiration ports 60) and be removed from the catheter system.

Figure 8:
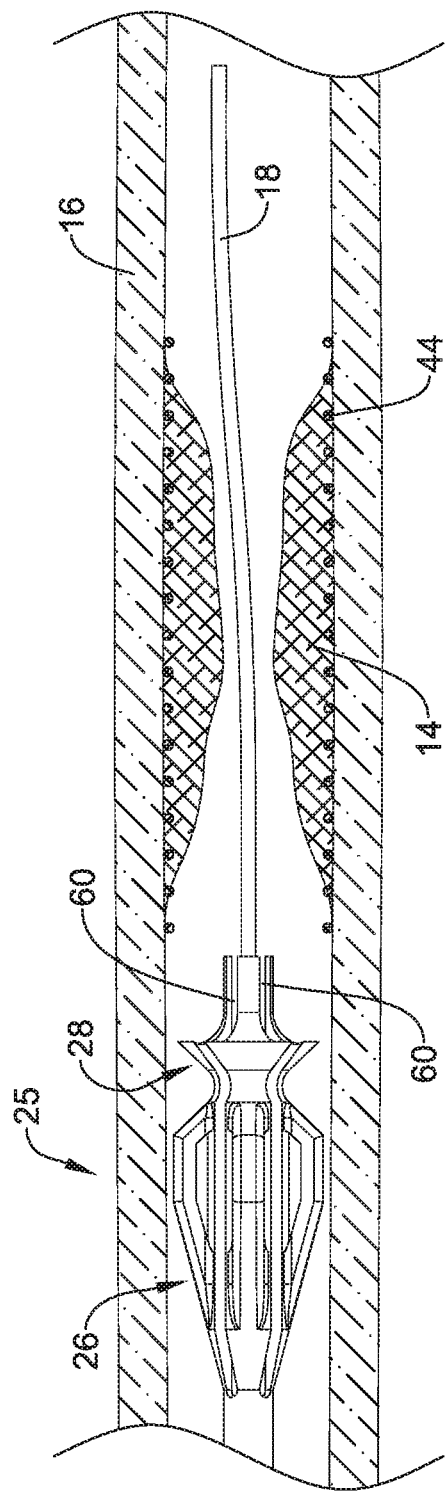
FIGS. 8 and 9 illustrate aspects of an exemplary method of treating an occlusion at a target site with an alternative medical device.

FIG. 8 shows another example atherectomy medical device 25. Atherectomy device 25 may operate in a similar fashion as example atherectomy medical device 24 described above. However, medical device 25 in FIG. 8 may operate in a "push" configuration.

In some instances the push configuration of atherectomy device 25 may be defined by "flipping" or "reversing" the position of both the cutting member 28 and the sizing member 26 as compared to the pull configuration. In other words, the cutting member 28 may be positioned distal of the sizing member 26. In the push configuration, the distal tip 50 (as described with respect to the pull configuration in FIG. 1) may be coupled to the distal end region of the cutting member 28. Further, aspiration ports 60 (as described with respect to FIG. 1) may be positioned near the distal end of atherectomy device 25, such as distal of the cutting member 28 and/or through the distal tip 50. In other words, the aspiration ports 60 may be in a forward-facing position as atherectomy device 25 is pushed through lesion 14 in a proximal to distal direction.

For example, FIG. 8 shows device 25 positioned proximal to example lesion 14 and stent 44 (or, as shown in FIG. 8, a lesion developed within a stent), with aspiration ports 60 leading as the device 25 is advanced distally toward lesion 14. Once positioned proximal to a lesion 14 and/or stent 44, cutting member 28 and sizing member 26 may be radially expanded and then atherectomy device 24 may be pushed and/or advanced in a distal direction through the lesion 14 and/or stent 44.

Similar to that discussed above with respect to the "pull" configuration, sizing member 26 may limit the radial expansion of cutting member 28. In other words, the radial expansion of cutting member 28 is limited by sizing member 26 to a diameter less than the inner diameter of the stent 44. For example, sizing member 26 may limit the radial expansion of cutting member 28 such that cutting member 28 (when advanced through a lesion developed within a stent) may excise the lesion 14 without damaging the stent 44.

In some instances (such as that shown in FIG. 9), sizing member 26 may be positioned proximal to cutting member 28 during a cutting procedure. Further, cutting member 28 may engage, enter, and/or pass through an occlusion and/or stent before the trailing sizing member 26 engages, enters and/or passes through the occlusion and/or stent. Thus, sizing member 26 may engage a portion of the vessel not obstructed by the occlusion and/or a portion of the vessel in which the occlusion has already been removed (by the cutting member 28, for example) to control the size of the cutting member 28 to an appropriate diameter.

For example, a physician may manipulate a proximal portion of elongate shaft 30 and push atherectomy device 25 in a proximal to distal direction toward and through the lesion 14. In other words, a physician manipulating atherectomy device 25 may push cutting member 28 closer and in contact with lesion 14. Further, as cutting member 28 is drawn closer to lesion 14, sizing member 26 may limit the radial expansion of cutting member 28 such that cutting member 28 does not contact any portion of the stent 44 and/or does not expand to a diameter greater than an inner diameter of the stent 44. Thus, the sizing member 26 may limit expansion of the cutting member 28 to a diameter less than an inner diameter of the stent 44.

Figure 9:
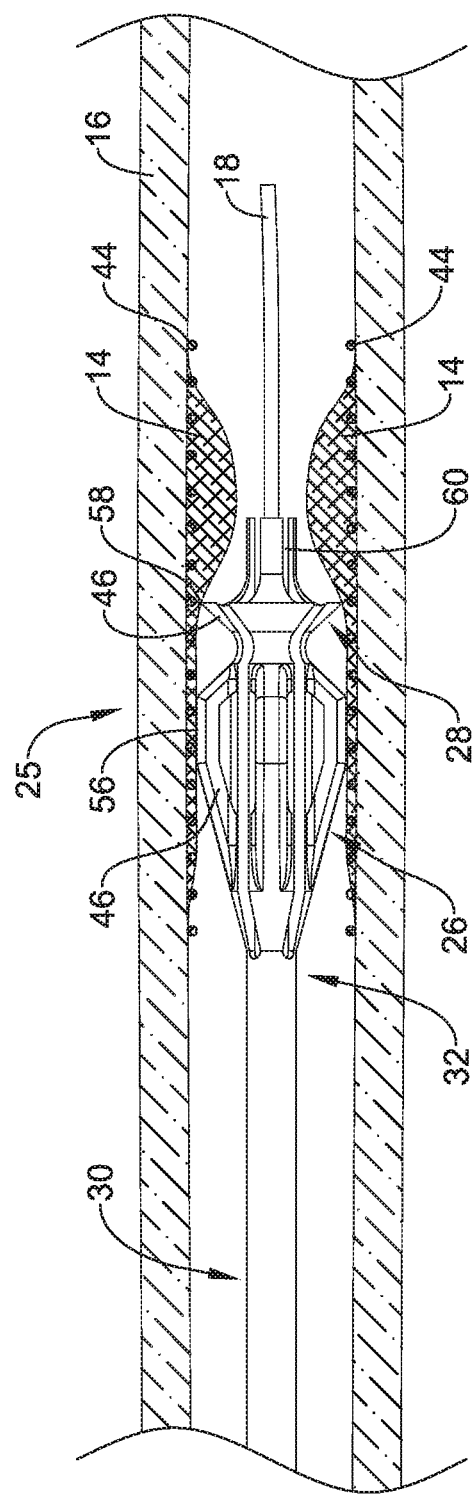

FIG. 9 shows atherectomy device 25 after having been pushed and/or advanced in a distal direction into example stent 44. Further, FIG. 9 shows cutting member 28 positioned along example lesion 14 (and within example stent 44). As can be appreciated from FIG. 9, cutting member 28 has cut and/or excised a portion of example lesion 14. Furthermore, FIG. 9 shows the outermost extent 56 of strut member 46 positioned against the inner surface of stent 44. As described above and shown in FIG. 9, the outermost extent 58 of example cutting blade 48 extends to a position radially inward from the interior surface of stent 44. In other words, the radial expansion of cutting member 28 is limited by sizing member 26 to a diameter less than the inner diameter of the stent 44.

Because sizing member 26 may be positioned proximal to cutting member 28 during a cutting procedure, it may engage a portion of the vessel not obstructed by the occlusion and/or a portion of the vessel in which the occlusion has already been removed (by the cutting member 28, for example). Thus, sizing member 26, when trailing the cutting member 28 in the direction of cutting through the lesion 14, may be expanded in an unobstructed portion of the body lumen to thereby adjust the cutting member 28 to an appropriate diameter slightly less than the unobstructed lumen of the vessel and/or stent 44.

In some instances, the cutting member 28 may be rotated as the cutting member 28 is drawn through the lesion 14, such as by rotating the elongate shaft 30 and/or a drive shaft passing through the elongate shaft 30. In other instances, no rotation of the cutting member 28 may be performed while passing the cutting member 28 through the lesion 14.

Additionally, atherectomy device 25 may aspirate excised tissue as device 25 is advanced through the vasculature. For example, as shown in FIG. 9, as cutting member 28 cuts and/or excises tissue while being pushed through lesion 14, excised tissue may be sucked into aspiration ports 60. Further, the excised tissue may travel through aspiration ports 60, lumen 64 of cutting member 28, lumen 62 of sizing member 26 and lumen 54 of elongate shaft 30 and be removed from the catheter system.

It is contemplated that lumen 52 of the distal tip 50, lumen 62 of the sizing member 26, lumen 64 of the cutting member 28 and lumen 54 of the elongate shaft 30 may be sized such that they can accept a guidewire 18 and/or the dilator 22 discussed above with respect to FIGS. 1-2, for example.

In addition to operating as described in the examples herein, it is contemplated that one or more portions of the atherectomy devices in the forgoing examples may rotate as they are pulled, pushed, advanced and/or manipulated in the vasculature. Furthermore, the cutting portions, alone or in combination with the sizing member, may rotate independently of the elongate shaft 30.

Figure 10:
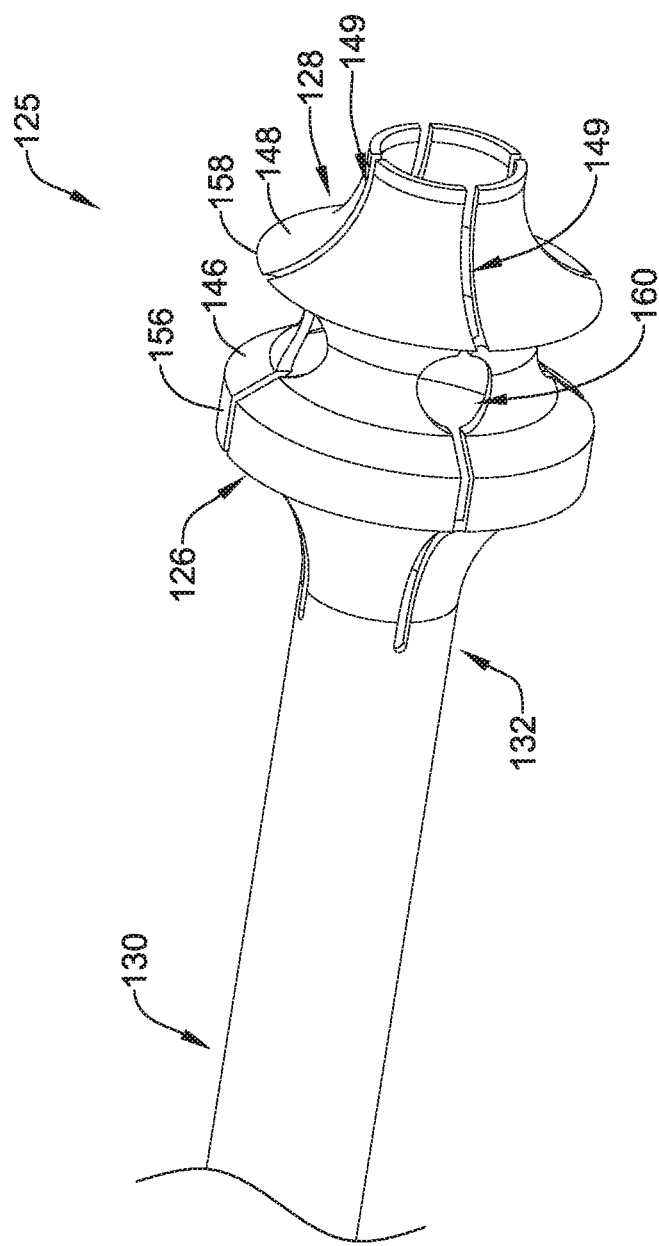
FIG. 10 is a perspective view of an alternate example medical device.

FIG. 10 shows another example atherectomy device 125. Similar to atherectomy device 25 above, device 125 may operate in a push configuration, with a sizing member 126 positioned proximal of the cutting member 128. As shown in FIG. 10, a proximal end region of sizing member 126 may be coupled to a distal end region 132 of elongate shaft 130. Further, a distal end region of sizing member 126 may be coupled to a proximal end region of cutting member 128.

The operation of atherectomy device 125 may be similar to that described above with respect to atherectomy device 25. For example, sizing member 126 may include one or more expandable members 146 spaced around a central longitudinal axis and having an outermost extent 156. Further, cutting member 128 may include one or more cutting blades 148 spaced around a central longitudinal axis and having an outermost extent 158. Both expandable members 146 and cutting blades 148 may be separated by channels 149, allowing for independent radial expansion/contraction of each expandable member 146 cutting blade 148 pair. Further, the cutting blades 148 may be longitudinally aligned with expandable members 146. Channels 149 may be in fluid communication with an aspiration lumen extending through the elongate shaft 130 for aspirating particulate from the treatment site.

Similar to embodiments described above, a constant radial offset may exist between outermost extent 156 of the sizing member 126 and outermost extent 158 of the cutting member 128. Furthermore, and similar embodiments described herein, each cutting blade 148 aligned with an associated expandable member 146 may flex independently of one another as the device is advanced through the vasculature.

FIG. 10 shows aspiration ports 160 positioned between sizing member 126 and cutting member 128. As shown in FIG. 10, aspiration ports 160 may be spaced around a central longitudinal axis of device 125 and may be substantially circular in shape. However, in other embodiments aspiration ports 160 may be ovular, square, triangular or any other desired shape.

Additionally, and similar to that described above, elongate shaft 130, sizing member 126 and cutting member 128 may all include a central lumen in fluid communication with one another. Further, the alignment of the channels 149 with aspiration ports 160, the central lumens of sizing member 126, cutting member 128 and elongate shaft 130 may provide a generally free-flowing path for tissue (e.g. lesion material) to be aspirated after having been excised by cutting blades 148.

Furthermore, it is contemplated that the central lumens of sizing member 126, cutting member 128 and elongate shaft 130 may be sized such that they can accept a guidewire and/or the dilator discussed above with respect to FIG. 5, for example.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An atherectomy device, comprising:
   an elongate shaft having a proximal end region, a distal end region and a lumen extending therein;
   a cutter positioned adjacent the distal end region of the elongate shaft, wherein the cutter is radially expandable and includes an outermost radial extent, wherein the cutter includes a plurality of blade members, wherein each blade member is radially expandable independent of the remainder of blade members; and
   a guide positioned adjacent the cutter, wherein the guide is radially expandable and includes an outermost radial extent, wherein the outermost radial extent of the cutter is offset a fixed radial distance from the outermost radial extent of the guide, wherein radial expansion of the cutter is directly proportional to radial expansion of the guide.

2. The device of claim 1, wherein the guide includes one or more struts extending along and away from a central longitudinal axis of the guide.

3. The device of claim 1, wherein the guide includes a distal tip and a lumen extending therein, and wherein the lumen of the guide is in communication with the lumen of the elongate shaft.

4. The device of claim 1, wherein the plurality of blade members are spaced around a central longitudinal axis of the cutter.

5. The device of claim 1, wherein the guide includes a plurality of struts, and wherein the struts are spaced around a central longitudinal axis of the guide.

6. The device of claim 5, wherein the plurality of blade members are spaced around a central longitudinal axis of the cutter.

7. The device of claim 6, wherein the plurality of blade members are longitudinally aligned with the plurality of struts.

8. The device of claim 6, wherein the struts have an outermost extent, wherein the blade members have an outermost extent, and wherein the outermost extent of the blade members is located closer to the central longitudinal axis than the outermost extent of the struts at any expanded state.

9. The device of claim 6, wherein one or more of the plurality of struts are configured to engage a portion of a vessel wall, and when the one or more of the plurality of struts is engaged with the vessel wall, the blade member aligned with the one or more of the plurality of struts is spaced radially away from the vessel wall a predetermined distance.

10. The device of claim 6, further comprising a plurality of base members, wherein each base member includes at least one strut and at least one blade member, and wherein each base member is configured to radially flex independently of the other base members.

11. The device of claim 6, further comprising one or more aspiration ports positioned at the distal end region of the elongate shaft, wherein the cutter includes a lumen extending therein, and wherein the aspiration ports are in communication with the lumen of the cutter.

12. The device of claim 1, further comprising one or more aspiration ports, wherein the one or more aspiration ports are in communication with the lumen of the elongate shaft.

13. The device of claim 1, wherein the lumen of the elongate shaft is sized to receive a guidewire or dilator therein when the atherectomy device is advanced over the guidewire or dilator.

14. An atherectomy device, comprising:
   an elongate shaft having a proximal end region, a distal end region and a lumen extending therein;
   a cutter positioned adjacent the distal end region of the elongate shaft, wherein the cutter is radially expandable and has an outermost radial extent, wherein the cutter includes a plurality of blade members, wherein one or more of the blade members can flex independently of the remaining blade members; and
   a guide positioned adjacent the cutter, wherein the guide is radially expandable and has an outermost radial extent, and wherein the atherectomy device includes a fixed radial offset, wherein the fixed radial offset is defined as a fixed radial distance between the outermost radial extent of the cutter and the outermost radial extent of the guide, wherein radial expansion of the cutter is directly proportional to radial expansion of the guide.

15. The device of claim 14, wherein the guide includes a plurality of struts, wherein the struts are spaced around a central longitudinal axis of the guide, and wherein the plurality of blade members are spaced around a central longitudinal axis of the cutter.

16. The device of claim 15, wherein the plurality of struts are longitudinally aligned with the plurality of blade members.

17. The device of claim 16, wherein one or more of the longitudinally aligned struts can flex independently of the remaining struts.

18. The device of claim 14, wherein the radial offset is defined such that the outermost radial extent of the cutter is positioned closer to a central longitudinal axis of the cutter than the outermost radial extent of the guide.

19. An atherectomy device, comprising:
- an elongate shaft having a proximal end region, a distal end region and a lumen extending therein;
- a guide positioned adjacent the distal end region of the elongate shaft, wherein the guide is radially expandable;
- a cutter positioned adjacent the guide, wherein the cutter is radially expandable, and wherein radial expansion of the cutter is directly proportional to radial expansion of the guide; and
- one or more channels extending between the elongate shaft, the guide and the cutter.

* * * * *